US009878295B2

(12) United States Patent
Marshall

(10) Patent No.: US 9,878,295 B2
(45) Date of Patent: Jan. 30, 2018

(54) FLUID IMPELLER FOR BIOPROCESSING

(71) Applicant: Pall Corporation, Port Washington, NY (US)

(72) Inventor: Glenn P. Marshall, Portsmouth (GB)

(73) Assignee: Pall Corporation, Port Washington, NY (US)

( * ) Notice: Subject to any disclaimer, the term of this patent is extended or adjusted under 35 U.S.C. 154(b) by 351 days.

(21) Appl. No.: 14/684,705

(22) Filed: Apr. 13, 2015

(65) Prior Publication Data
US 2016/0296897 A1 Oct. 13, 2016

(51) Int. Cl.
| | | |
|---|---|---|
| *B01F 7/00* | (2006.01) | |
| *B01F 7/22* | (2006.01) | |
| *B01F 15/00* | (2006.01) | |
| *C12M 1/00* | (2006.01) | |
| *C12M 1/06* | (2006.01) | |
| *B01F 7/16* | (2006.01) | |

(52) U.S. Cl.
CPC .......... *B01F 7/00091* (2013.01); *B01F 7/162* (2013.01); *B01F 7/1695* (2013.01); *B01F 7/22* (2013.01); *B01F 15/0085* (2013.01); *C12M 23/14* (2013.01); *C12M 27/02* (2013.01); *C12M 27/18* (2013.01)

(58) Field of Classification Search
CPC ...... B01F 7/0091; B01F 15/0085; B01F 7/22; B01F 7/162; B01F 7/1695
USPC ........................................................ 366/244
See application file for complete search history.

(56) References Cited

U.S. PATENT DOCUMENTS

| | | | |
|---|---|---|---|
| 4,508,455 A | 4/1985 | Lerman et al. | |
| 4,840,905 A * | 6/1989 | Kearns | B01F 7/00641 |
| | | | 261/84 |
| 5,524,982 A | 6/1996 | Kruse et al. | |
| 7,296,925 B2 * | 11/2007 | Himmelsbach | B01F 7/00275 |
| | | | 366/330.3 |
| 8,277,114 B2 | 10/2012 | Higbee et al. | |
| 8,397,495 B2 | 3/2013 | Salanta et al. | |
| 8,894,756 B2 | 11/2014 | Galliher et al. | |
| 2008/0031088 A1 | 2/2008 | Ukita | |
| 2009/0176301 A1 | 7/2009 | Oldenburg et al. | |
| 2012/0045834 A1 | 2/2012 | Jones et al. | |
| 2013/0003495 A1 | 1/2013 | Pyddoke | |
| 2015/0117142 A1 | 4/2015 | Staheli et al. | |
| 2015/0151261 A1 | 6/2015 | Isailovic | |

FOREIGN PATENT DOCUMENTS

| | | |
|---|---|---|
| CA | 2 929 904 A1 | 5/2015 |
| DE | 10 2006 053339 A1 | 5/2008 |
| DE | 10 2013 018690 A1 | 5/2015 |
| EP | 2 374 529 A2 | 10/2011 |
| JP | 61-500418 A | 3/1986 |

(Continued)

OTHER PUBLICATIONS

European Patent Office, Extended European Search Report in counterpart European Patent Application No. 16156536.1, dated Aug. 25, 2016.

*Primary Examiner* — Tony G Soohoo
*Assistant Examiner* — Anshu Bhatia
(74) *Attorney, Agent, or Firm* — Leydig Voit & Mayer

(57) ABSTRACT

Fluid impellers for biocontainers, and bioprocessing units including the impellers and biocontainers, and methods of using the impellers, are disclosed.

4 Claims, 12 Drawing Sheets

(56) References Cited

FOREIGN PATENT DOCUMENTS

| | | |
|---|---|---|
| JP | 07-232232 A | 9/1995 |
| JP | 2013-522024 A | 6/2013 |
| JP | 2013-223849 A | 10/2013 |
| JP | 2015-110223 A | 6/2015 |
| WO | WO 2013/075236 A1 | 5/2013 |

* cited by examiner

US 9,878,295 B2

FLUID IMPELLER FOR BIOPROCESSING

BACKGROUND OF THE INVENTION

The preparation of fluids, particularly solutions and suspensions in the pharmaceutical and biopharmaceutical industries, typically involves thorough mixing to provide the desired distribution of ingredients in the product. Many mixing operations are carried out in bioreactor bags with a mixing impeller mounted near the base of the vessel. A variety of impellers with different size impeller hubs, impeller blades and/or blade configurations can be used for mixing.

However, there is a need for improved impellers and bioreactor bags including impellers.

The present invention provides for ameliorating at least some of the disadvantages of the prior art. These and other advantages of the present invention will be apparent from the description as set forth below.

BRIEF SUMMARY OF THE INVENTION

In accordance with an embodiment of the present invention, an impeller for a biocontainer comprises (a) a hub including a top end and a bottom end, and at least first and second impeller arm slots arranged vertically and extending from the top end toward the bottom end; (b) at least first and second impeller blades extending from the hub, each impeller blade comprising a blade face, an arm having a first end and a second end and a notch between the first end and the second end, wherein the first end is adjacent the blade face, and the second end extends into an impeller slot, the arm being engaged in the slot, and wherein the second end of the first impeller blade arm engages with the notch of another impeller blade arm.

In another embodiment a bioprocessing unit is provided comprising a bioreactor bag (biocontainer) and an agitator comprising the impeller comprising the hub and impeller blades, and a housing assembly, as well as a rotatable shaft comprising a cylindrical element having a first end and a second end, the shaft having a vertical rotational axis, the shaft passing through the bottom wall of the biocontainer such that the second end extends exterior to the bottom wall; the hub mounted on the first end of the rotatable shaft, the hub including a top end and a bottom end and at least first and second impeller arm slots arranged vertically and extending from the top end toward the bottom end; wherein the housing assembly is coupled to the bottom wall of the biocontainer, the housing assembly sealingly supporting the rotatable shaft, wherein the second end of the shaft passes through the housing assembly.

A method of preparing a mixed fluid used in bioprocessing according to another embodiment of the invention method comprises (a) passing at least one fluid and at least one component to be mixed with the fluid through at least one port into a biocontainer comprising a closed container having an interior volume, the container comprising a bottom wall, a top wall, at least one wall, the side wall(s) being joined to the top wall and the bottom wall; and at least the inlet port, and a drain port, the drain port being arranged in the bottom wall, wherein the biocontainer further comprises the agitator; and, (b) rotating the impeller, and mixing the at least one fluid and the at least one component to be mixed with the fluid, and producing the mixed fluid.

BRIEF DESCRIPTION OF THE SEVERAL VIEWS OF THE DRAWING(S)

Figure 4A:
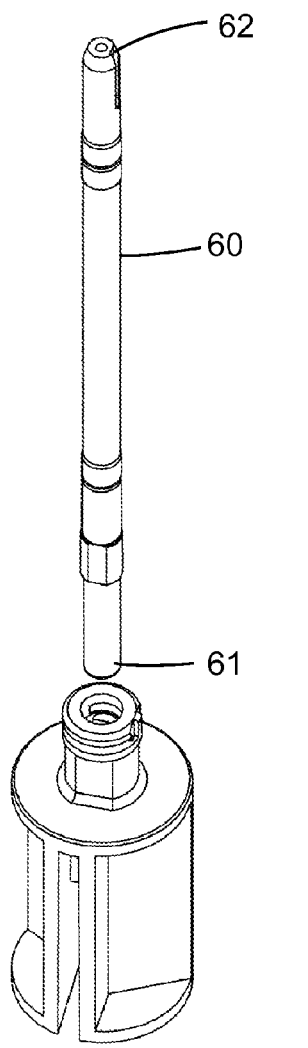
Figure 4B:
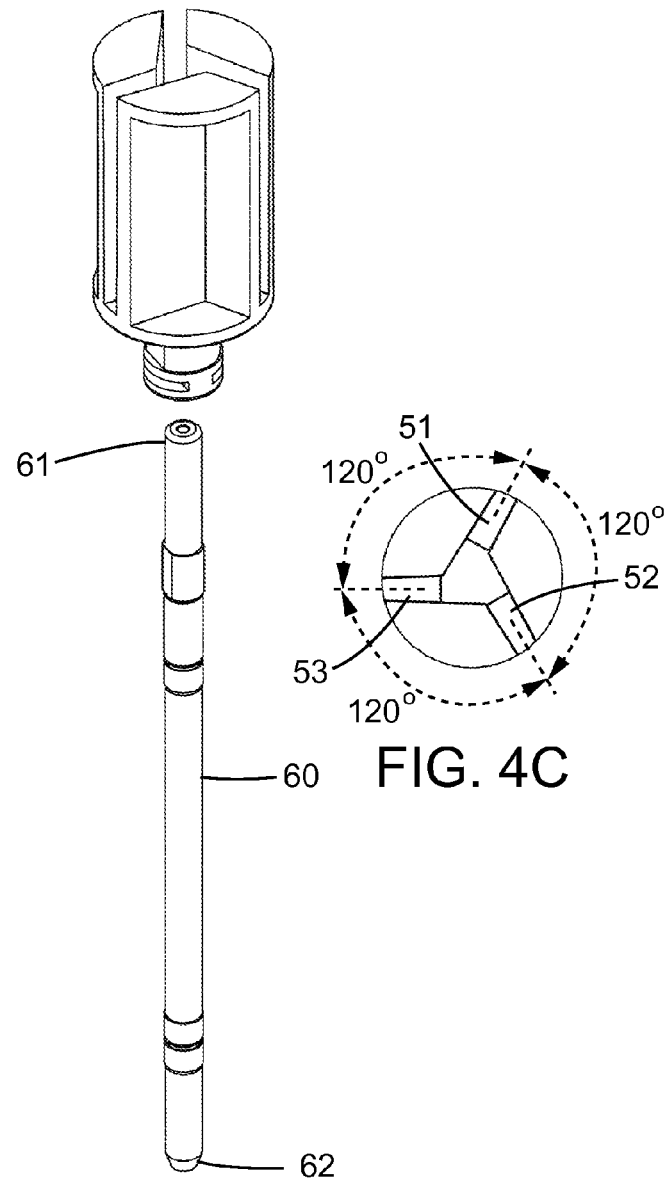
Figure 4C:
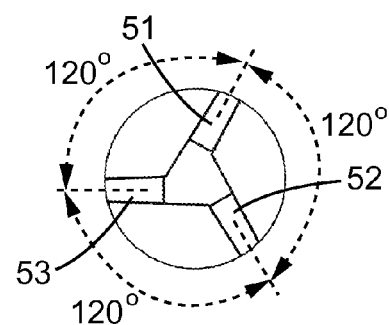
Figure 4D:
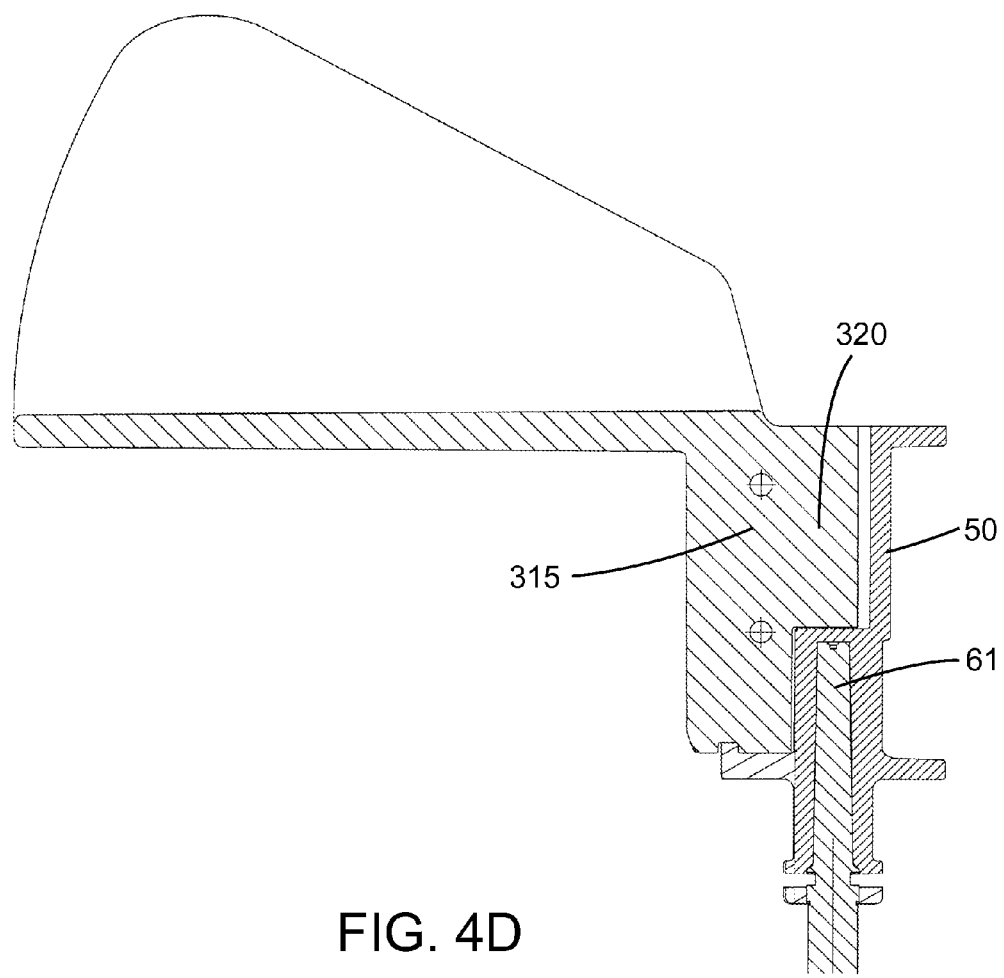
Figure 4E:
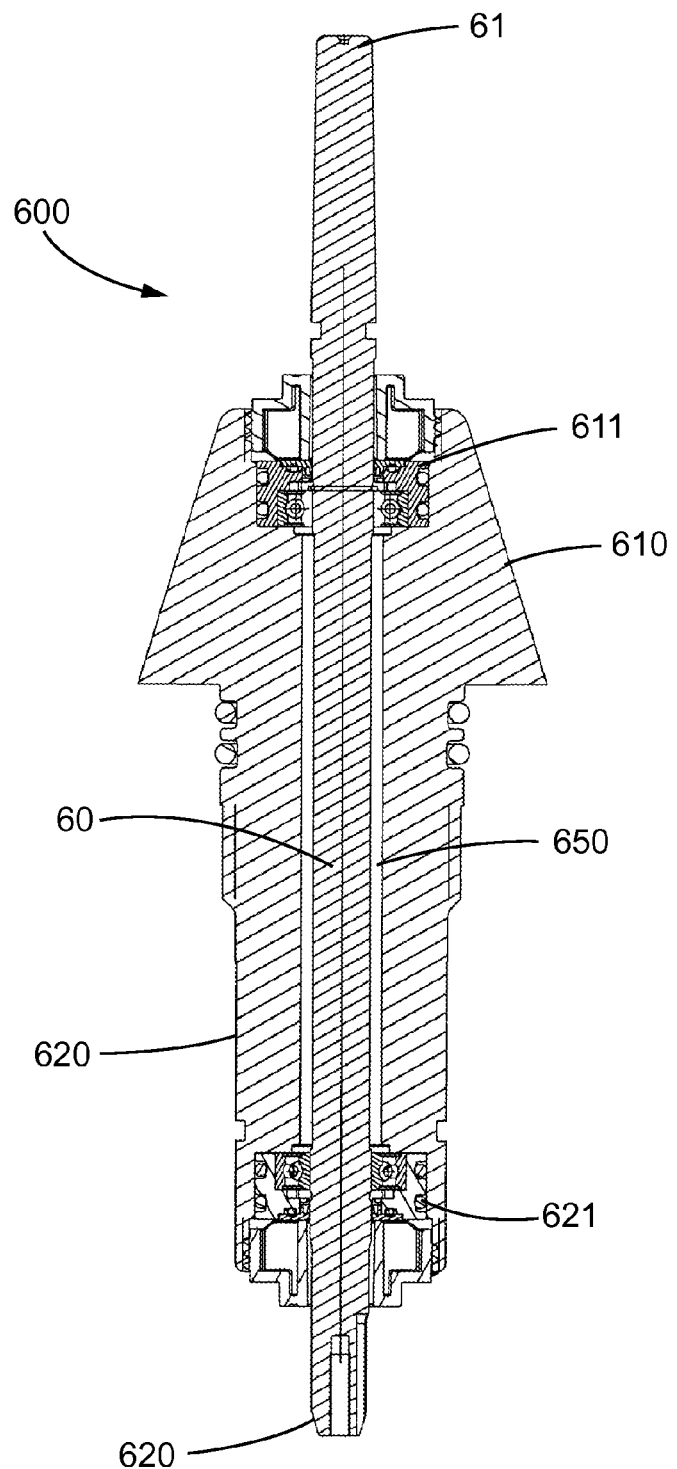

FIGS. 4A and 4B show, respectively, exploded bottom perspective, and top perspective, views of a hub and a shaft for driving (rotating) the hub. FIG. 4C shows a top view of the hub, wherein the slot has three slots (each slot for receiving an impeller blade), each slot positioned at a 120° angle around the center of the hub. FIG. 4D shows a partial cross-sectional view of a impeller blade, as well as the hub and shaft. FIG. 4E shows a cross-section view of an impeller housing assembly including the shaft.

Figure 5A:
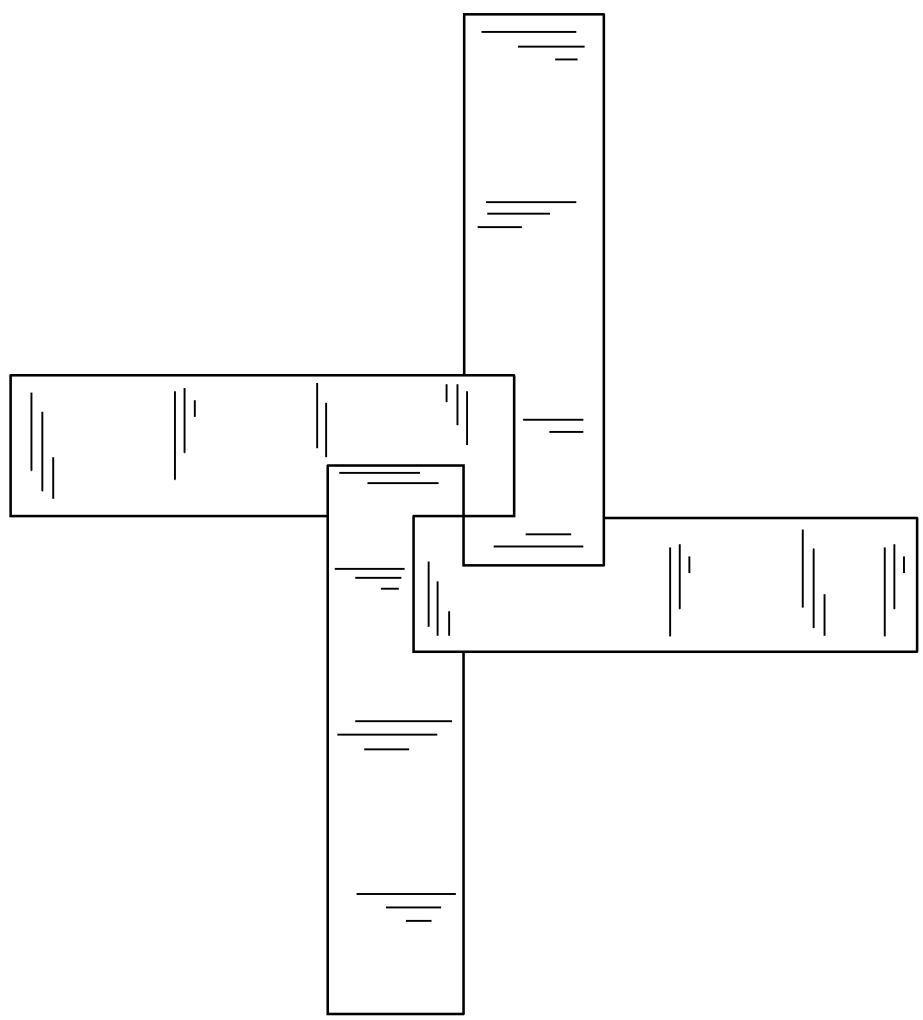
Figure 5B:
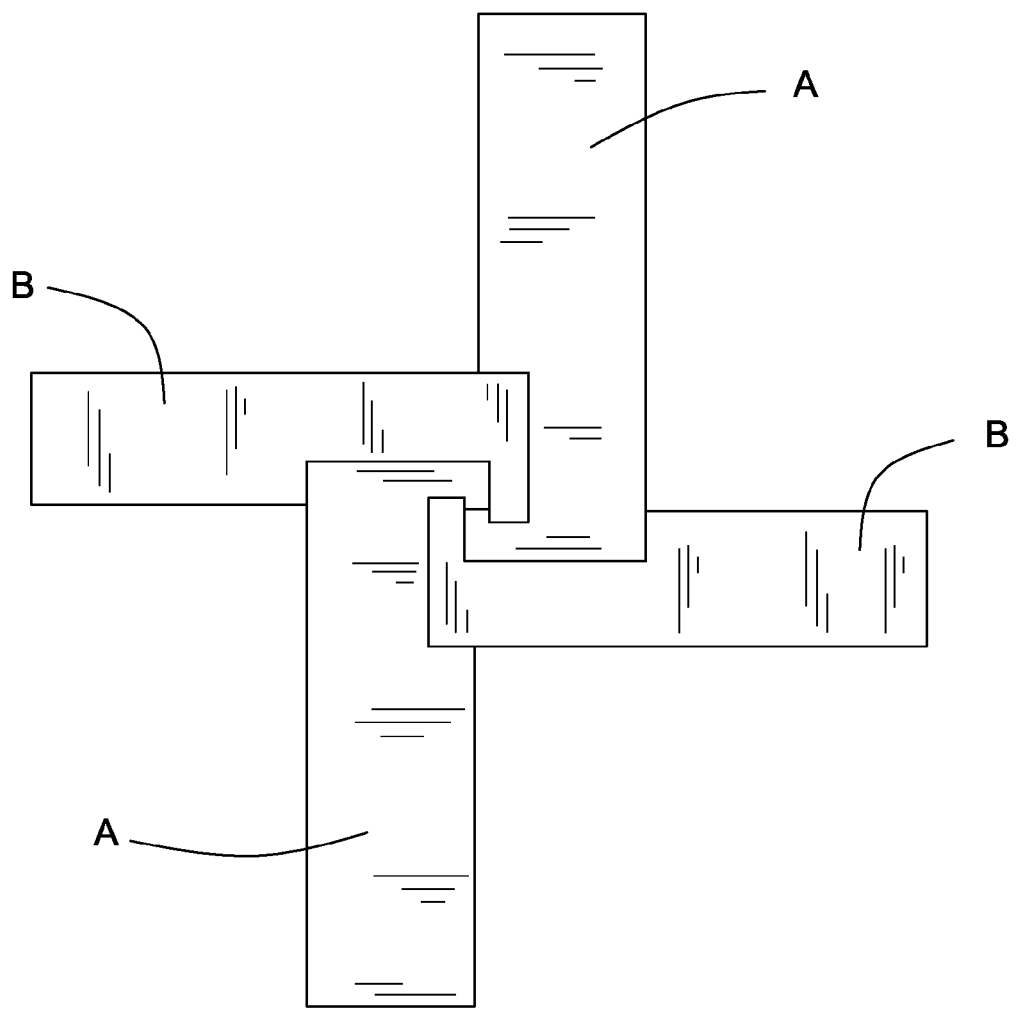

FIGS. 5A and 5B show, diagrammatically, 4 impeller blades wherein the end of one impeller blade arm engages with a notch of another impeller blade arm. FIG. 5A shows 4 identical blades, and FIG. 5B shows 2 different blades, wherein the blades within a pair are identical.

Figure 6A:
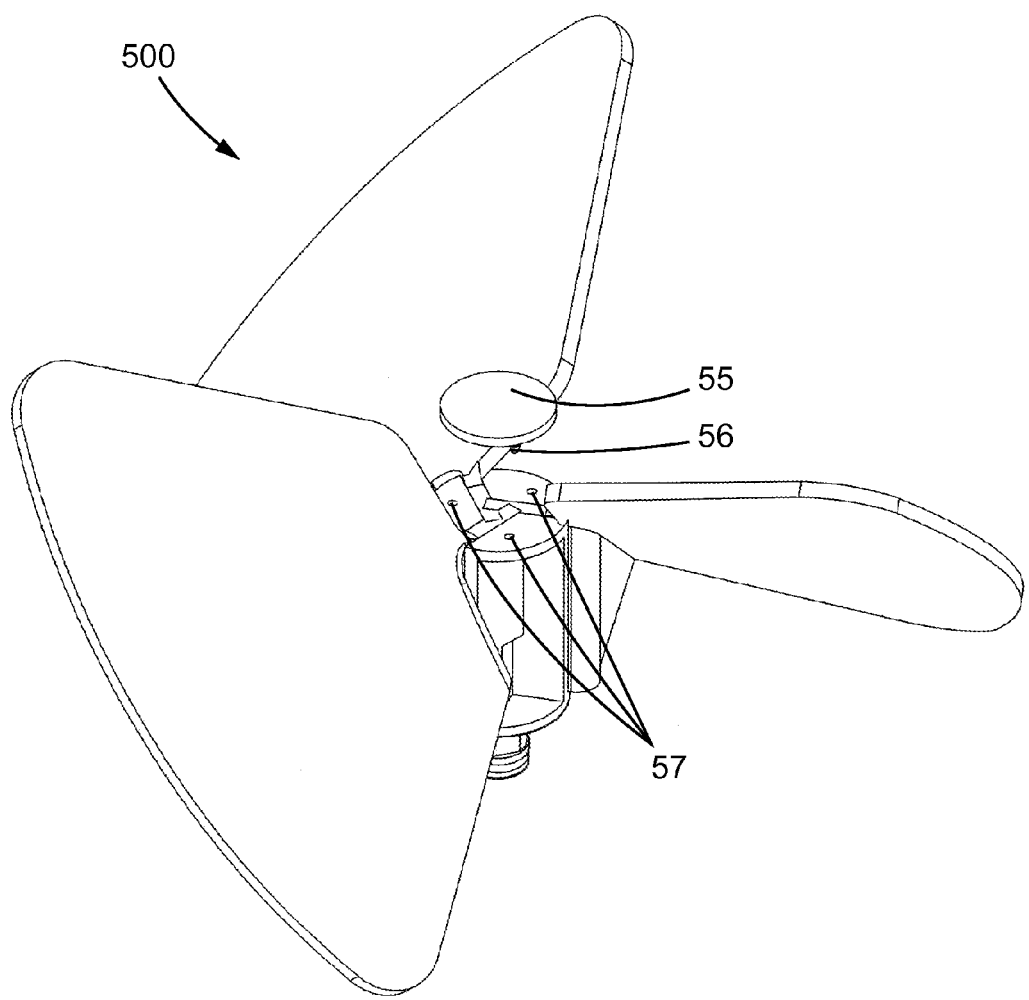
Figure 6B:
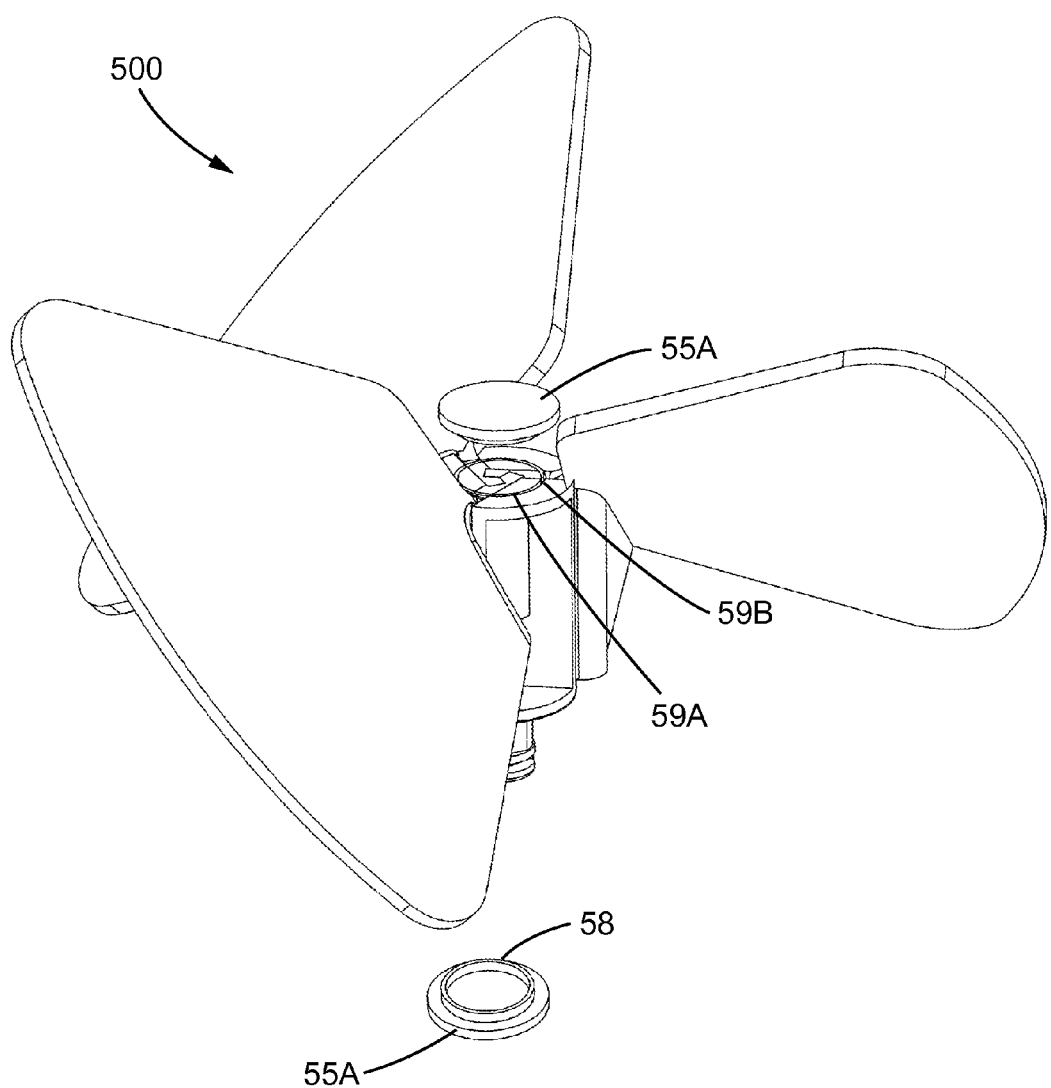

FIGS. 6A and 6B show an impeller comprising 3 impeller blades according to another embodiment of the invention, the impeller further comprising a hub cap that engages with the hub and further holds the blades in position. FIG. 6A shows a cap including pegs that can be "snap fit" into receiving holes the hub, and FIG. 6B shows a cap with a tab that can be welded into a groove present in the hub and the blades.

Figure 1:
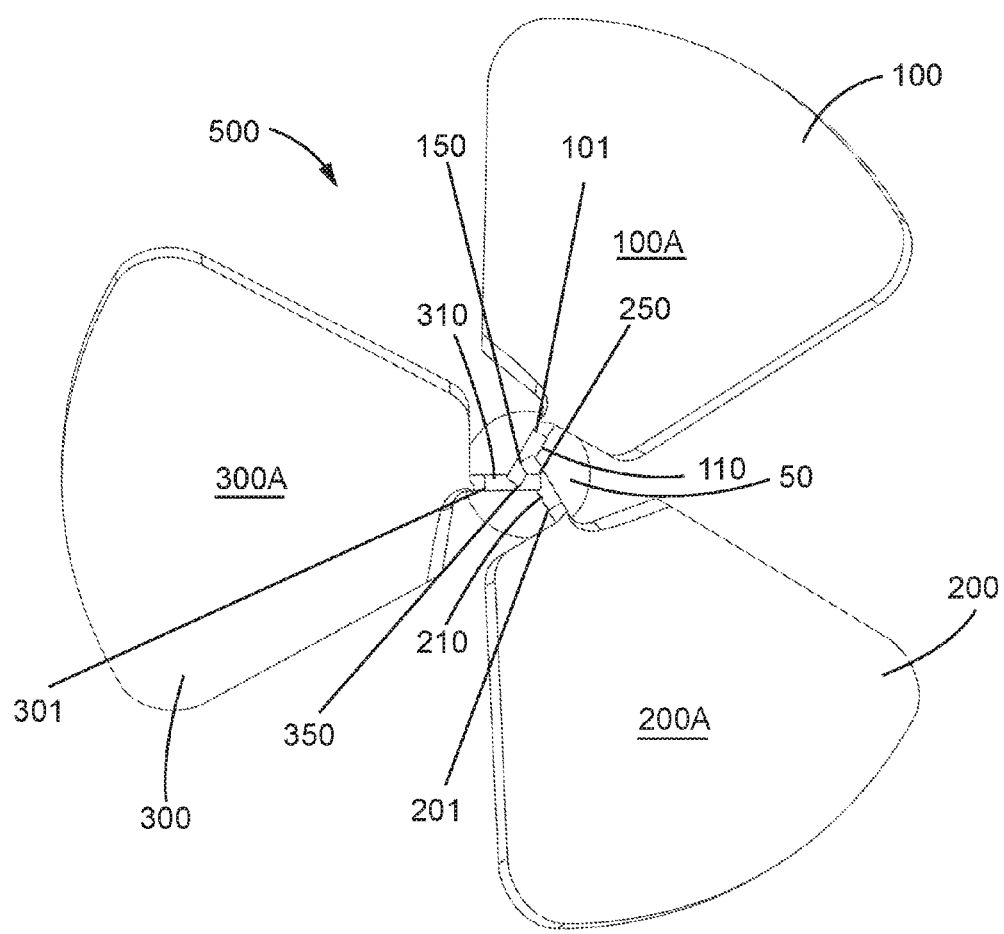
FIG. 1 shows a top view of an impeller comprising a hub and 3 impeller blades according to an embodiment of the present invention, wherein the blades are engaged in slots in the hub, and the blades each have faces, arms and notches, and an end of one impeller blade arm engages with a notch of another impeller blade arm.
Figure 7:
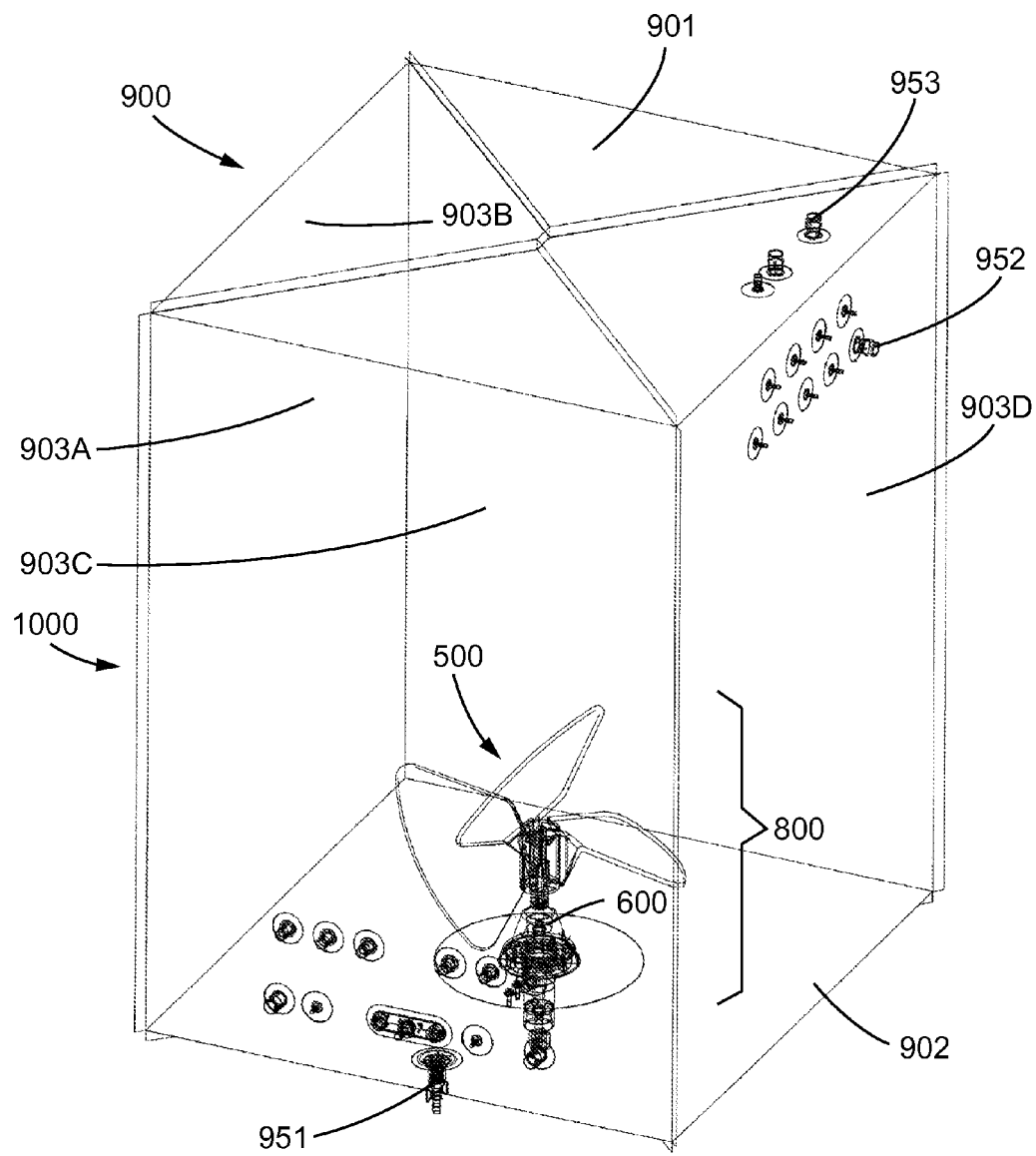

FIG. 7 shows an embodiment of a bioprocessing unit comprising a biocontainer and the impeller shown in FIG. 1.

DETAILED DESCRIPTION OF THE INVENTION

In accordance with an embodiment of the present invention, an impeller for a biocontainer comprises (a) a hub including a top end and a bottom end, and at least first and second impeller arm slots arranged vertically and extending from the top end toward the bottom end; (b) at least first and second impeller blades extending from the hub, each impeller blade comprising a blade face, an arm having a first end and a second end and a notch between the first end and the second end, wherein the first end is adjacent to the blade face, and the second end extends into an impeller slot, the arm being engaged in the slot, and wherein the second end of the first impeller blade arm engages with the notch of another impeller blade arm.

In an embodiment, the hub includes a third impeller arm slot arranged vertically, the impeller further comprising a third impeller blade comprising a blade face, an arm having first end and a second end and a notch between the first end and the second end, extending into an impeller slot, the arm being engaged in the slot, wherein the second end of the first impeller blade arm engages with the notch of the third impeller blade arm, the second end of the third impeller blade arm engages with the notch of the second impeller blade arm, and the second end of the second impeller blade arm engages with the notch of the first impeller blade arm.

In another embodiment a bioprocessing unit is provided comprising a bioreactor bag (biocontainer) and an agitator comprising the impeller comprising the hub and impeller blades, and a housing assembly, as well as a rotatable shaft comprising a cylindrical element having a first end and a second end, the shaft having a vertical rotational axis, the shaft passing through the bottom wall of the biocontainer such that the second end extends exterior to the bottom wall; the hub mounted on the first end of the rotatable shaft, the hub including a top end and a bottom end and at least first and second impeller arm slots arranged vertically and extending from the top end toward the bottom end; wherein the housing assembly is coupled to the bottom wall of the biocontainer, the housing assembly sealingly supporting the rotatable shaft, wherein the second end of the shaft passes through the housing assembly.

A bioprocessing unit for use in bioprocessing according to another embodiment of the invention comprises (a) a biocontainer comprising a closed container having an interior volume suitable for containing fluid, the container comprising a bottom wall, a top wall, at least one side wall, the side wall(s) being joined to the top wall and the bottom wall; and at least an inlet port, and a drain port, the drain port being arranged in the bottom wall, wherein the biocontainer further comprises (b) a rotatable agitator comprising (i) a rotatable shaft comprising a cylindrical element having a first end and a second end, the shaft having a vertical rotational axis, the shaft passing through the bottom wall of the biocontainer such that the second end extends exterior to the bottom wall; (ii) an impeller comprising a hub mounted on the first end of the rotatable shaft, the hub including a top end and a bottom end and at least first and second impeller arm slots arranged vertically and extending from the top end toward the bottom end; (iii) at least first and second impeller blades extending from the hub, each impeller blade comprising a blade face, an arm having a first end and a second end and a notch between the first end and the second end, wherein the first end is adjacent to the blade face, and the second end extends into an impeller slot, the arm being engaged in the slot, wherein the second end of one arm engages with the notch of another arm; and (iv) a housing assembly coupled to the bottom wall of the biocontainer, the housing assembly sealingly supporting the rotatable shaft, wherein the second end of the shaft passes through the housing assembly.

In a preferred embodiment of the bioprocessing unit, the impeller comprises a third impeller blade, wherein hub includes a third impeller arm slot arranged vertically, the impeller further comprising the third impeller blade comprising a blade face, an arm having first end and a second end and a notch between the first end and the second end, extending into an impeller slot, the arm being engaged in the slot, wherein the second end of the first impeller blade arm engages with the notch of the third impeller blade arm, the second end of the third impeller blade arm engages with the notch of the second impeller blade arm, and the second end of the second impeller blade arm engages with the notch of the first impeller blade arm.

A method of preparing a mixed fluid used in bioprocessing according to another embodiment of the invention method comprises (a) passing at least one fluid and at least one component to be mixed with the fluid through at least one port into a biocontainer comprising a closed container having an interior volume, the container comprising a bottom wall, a top wall, at least one side wall, the side wall(s) being joined to the top wall and the bottom wall; and at least the inlet port, and a drain port, the drain port being arranged in the bottom wall, wherein the biocontainer further comprises the agitator; and, (b) rotating the impeller, and mixing the at least one fluid and the at least one component to be mixed with the fluid, and producing the mixed fluid.

Advantageously, the same hub design can be used with a variety of different blade sizes and configurations (e.g., different blade face angles), thus reducing cost.

Each of the components of the invention will now be described in more detail below, wherein like components have like reference numbers.

While embodiments of the impeller have at least two impeller blades, and can have any number of additional blades, in accordance with the embodiment shown in FIG. 1, the impeller 500 comprises a hub 50 and first, second, and third, impeller blades 100, 200, 300, extending from the hub. Using FIGS. 1, 2B, and 3 for illustrative reference (FIGS. 2B and 3 showing blade 300, wherein blades 100 and 200 have the same structure as blade 300), each impeller blade comprises a blade face 100A, 200A, 300A, an arm 110, 210, 310, having a first end 101, 201, 301, and a second end 102, 202, 302, and a notch 150, 250, 350, between the first and second ends, wherein the first end is adjacent to (illustrated as also connected to) the blade face, and the second end extends into an impeller slot 51, 52, 53, in the hub. In the embodiment illustrated in FIGS. 2A and 2B, the hub includes a top end 50A and a bottom end 50B, and the impeller slots are vertically arranged, extending from the top end toward the bottom end.

Figure 2A:
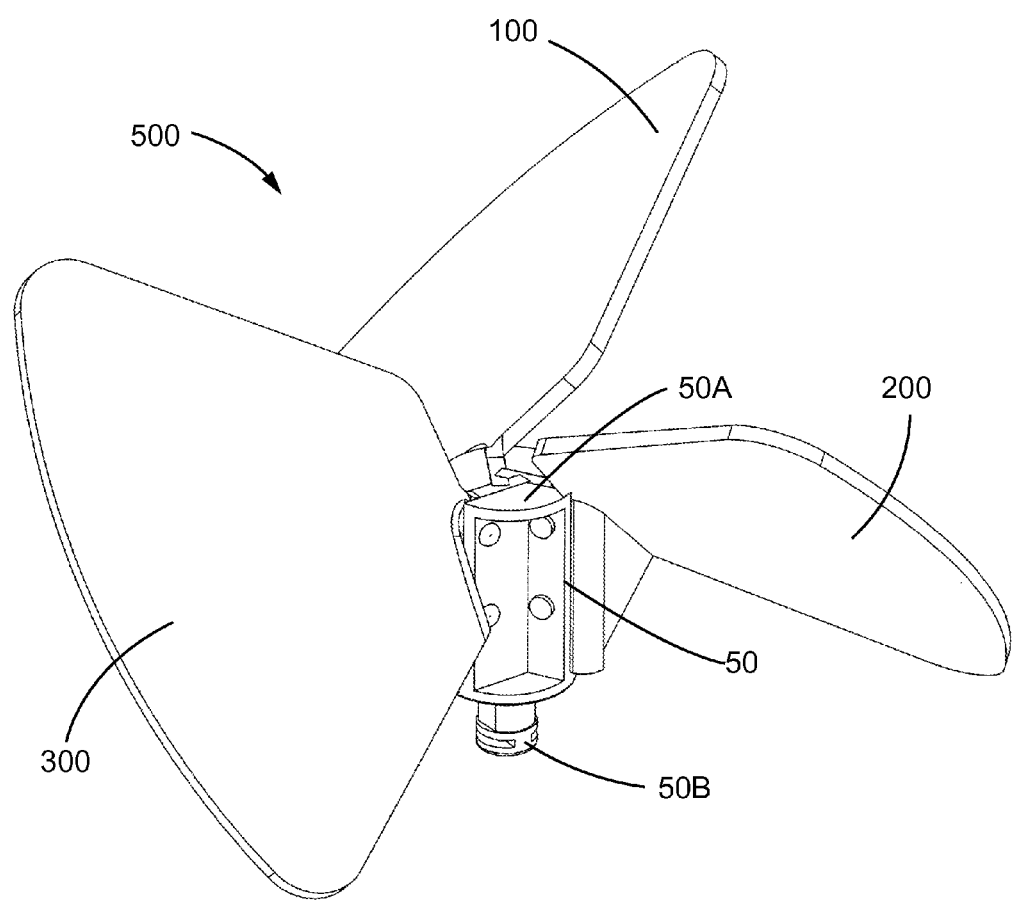
FIG. 2A shows a perspective view of the impeller shown in FIG. 1 (the illustrated hub including bolts or rivets passing through the blades further holding the blades in position)
Figure 2B:
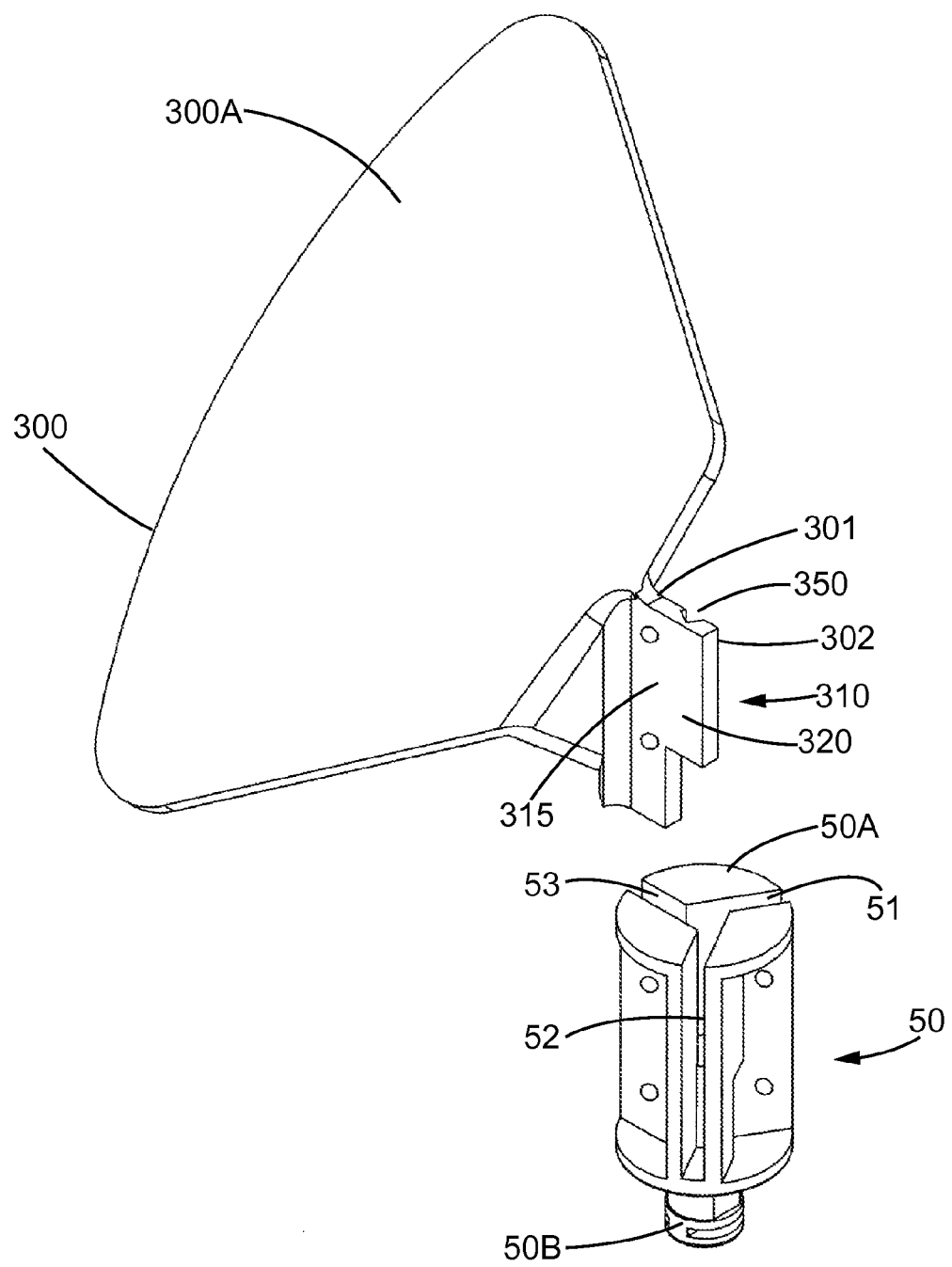
FIG. 2B shows a partially exploded view with 2 of the impeller blades removed.
Figure 3:
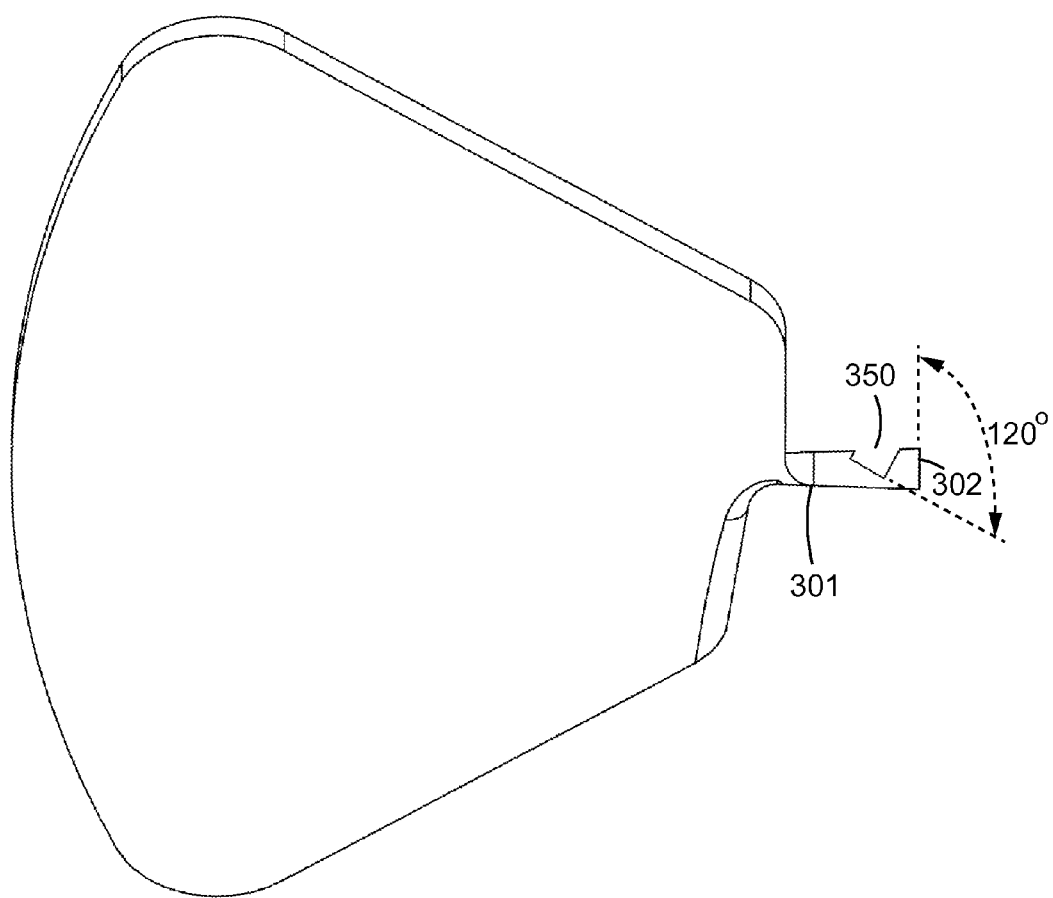
FIG. 3 shows a top view of the impeller blade shown in FIG. 2, also showing an impeller blade arm having a notch having an angle of 120°.

Using the embodiment of the impeller illustrated in FIG. 2B showing blade 300 for reference, each arm includes an extension 115 (blade 100), 215 (blade 200), and 315 (blade 300), substantially filling the length of the hub slot from the top end toward the bottom end, and in the embodiment illustrated in FIGS. 2A and 2B the hub and extensions each include through-holes, e.g., for a rivet or bolt for further securing the blades to the hub. However, as shown in FIGS. 2B and 4D, the extension can include a leg 320 (e.g., a portion of the extension including the notch) that does not substantially fill the length of the hub slot from the top end toward the bottom end toward the outer edge of the hub.

As noted above, the impeller has two or more impeller blades. FIGS. 1, 2A, 6A, 6B, and 7 show 3 blades, and FIGS. 5A and 5B show 4 blades. The angle of the notch in the impeller arm between the first and second ends of the arm is typically 360° divided by the number of blades. Thus, for example, FIG. 3 (showing an impeller blade for use in a 3 blade embodiment of the impeller) shows a notch having an angle of 120°. Similarly, the slots in the hub are positioned at equal angles around the center of the hub. Thus, for example, FIG. 4C, showing a hub with 3 slots, shows slots positioned at 120° angles around the center of the hub. With respect to the 4 blade embodiments illustrated in FIGS. 5A and 5B, the angles would preferably be 90°.

Preferably, in those embodiments having 2 impeller blades, or odd numbers of blades (3, 5, 7, etc.), all of the blades are identical. For example, the blades are identical in the embodiments shown in FIGS. 1, 2A, 5A, 6A, 6B, and 7. However, in those embodiments having even number of 4 or more blades (4, 6, 8, etc.), 2 different blades can be used, wherein the blades within a pair are identical. For example, the embodiment shown in FIG. 5B shows 2 different blades ("A" and "B"), wherein the blades within a pair (A, A; B, B) are identical.

The impeller blades can otherwise have any suitable configuration. For example, while FIG. 2B shows a blade 300 having a face 300A angled at about 45°, the invention is not so limited.

In the embodiment illustrated in FIGS. 2A and 2B, the hub and the impeller blade extensions each include through-holes, e.g., for a rivet or bolt for further securing the blades to the hub. However, in other embodiments, through-holes and/or rivets and/or bolts are not required. For example, in accordance with the embodiments shown in FIGS. 6A and 6B, the impeller further comprises a hub cap that engages with the top end of the hub and further holds the blades in position. FIG. 6A shows a cap 55 including pegs (only one peg 56 is shown) that can be "snap fit" into receiving holes 57 in the hub, and FIG. 6B shows a cap 55A with a tab 58 that can be welded into a groove present in the hub 59A and the blades 59B.

Embodiments of impellers according to the invention can be used with a variety of bioreactor bags having different configurations and/or volumes, wherein, using FIGS. 4A and 4B for general reference, a rotatable shaft 60 comprising a cylindrical element having a first end 61 and a second end 62, the shaft having a vertical rotational axis, drives (rotates) the impeller, wherein a first end of the shaft is inserted into the hub 50 (located in the interior volume of the bioreactor bag), and the second end of the shaft extends exterior to the bottom wall of the bioreactor, and the second end is attached, directly, or indirectly, to a motor that rotates the shaft.

For example, an agitator can be provided in accordance with an embodiment of the invention, the agitator comprising the impeller comprising the hub and impeller blades, and a housing assembly, as well as a rotatable shaft comprising a cylindrical element having a first end and a second end, the shaft having a vertical rotational axis, the shaft passing through a bottom wall of a biocontainer such that the first end extends into the interior volume of the container and the second end extends exterior to the bottom wall; the hub mounted on the first end of the rotatable shaft, the hub having a horizontal axis perpendicular to the vertical rotational axis of the shaft, the hub including a top end and a bottom end and at least first and second impeller arm slots arranged vertically and extending from the top end toward the bottom end; wherein the housing assembly is couplable to the bottom wall of the biocontainer, the housing assembly sealingly supporting the rotatable shaft, wherein the second end of the shaft passes through the housing assembly. Typically, the housing assembly comprises a bearing and at least one seal. As variety of housing assemblies are suitable. FIG. 4E shows an illustrative housing assembly 600 comprising an upper housing portion 610 comprising an upper portion seal assembly 611, and a lower housing portion 620 comprising a lower portion seal assembly 621 (each seal assembly comprising a central channel, a seal with an annular opening, and a bearing), and a central channel 650 passing through the seal housing assembly and the upper and lower housing portions. FIG. 4E also shows the rotatable shaft 60 having a first end 61 and a second end 62, in the central channel 650. The housing assembly can be mounted to a bioreactor bag via, for example, a locking ring (not shown).

The bioreactor bag (or biocontainer or bioprocessing container), which is flexible (e.g., plastic), can have any suitable form (e.g., cylindrical (having, for example, a single continuous side wall), square, or rectangular), and in FIG. 7 is illustrated as having a generally rectangular cuboid form with a plurality of side walls.

Embodiments of the bioreactor bag can have any suitable number and locations of ports, for example, one or more of any of the following ports: a liquid inlet port, a gas inlet port, a gas outlet port, a powder inlet port, an acid/base inlet port, a probe port, and/or a sample port.

FIG. 7 shows an embodiment of a bioreactor (or bioprocessing unit) 1000 comprising a bioreactor bag 900 (biocontainer) comprising a top wall 901, a bottom wall 902, and side walls 903A, 903B, 903C, and 903D, a drain port 951, a media inlet port 952, a vent filter connection port 953, and an agitator 800 comprising the impeller 500 comprising the hub 50 and first, second, and third impeller blades and a housing assembly 600, as well as a rotatable shaft 60 comprising a cylindrical element having a first end and a second end, the shaft having a vertical rotational axis, the shaft passing through the bottom wall 902 of the biocontainer such that the second end extends exterior to the bottom wall; the hub mounted on the first end of the rotatable shaft, the hub having a horizontal axis perpendicular to the vertical rotational axis of the shaft, the hub including a top end and a bottom end and at least first and second impeller arm slots arranged vertically and extending from the top end toward the bottom end; wherein the housing assembly is coupled to the bottom wall of the biocontainer, and the housing assembly sealingly supporting the rotatable shaft, wherein the second end of the shaft passes through the housing assembly.

A variety of fluids can be processed and/or prepared (including mixing) in accordance with embodiments of the invention. Applications include, for example, cell culture (e.g., including batch and fed-batch operations of suspension and adherent cell lines), preparing sterile fluids for the pharmaceutical and/or biopharmaceutical industries, including drugs, vaccines, and intravenous fluids, antibody- and/or protein-containing fluids, and/or fluids for the food and beverage industry. Fluids mixed according to embodiments of the invention can also used, for example, as media and/or buffers such as chromatography buffers.

For example, a method for preparing a mixed fluid used in bioprocessing comprises (a) passing at least one fluid and at least one component to be mixed with the fluid through one or more ports into a biocontainer, and (b) rotating the impeller, and mixing the at least one fluid and the at least one component to be mixed with the fluid, and producing the mixed fluid, which can be used as desired.

The following examples further illustrate the invention but, of course, should not be construed as in any way limiting its scope.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A bioprocessing unit for use in bioprocessing comprising:
   (a) a biocontainer comprising a closed container having an interior volume suitable for containing fluid, the container comprising a bottom wall, a top wall, at least one side wall, the at least one side wall being joined to the top wall and the bottom wall; and at least an inlet port, and a drain port, the drain port being arranged in the bottom wall, wherein the biocontainer further comprises:
   (b) a rotatable agitator comprising
      (i) a rotatable shaft comprising a cylindrical element having a first end and a second end, the shaft having a vertical rotational axis, the shaft passing through the bottom wall of the biocontainer such that the second end extends exterior to the bottom wall;
      (ii) an impeller comprising a hub mounted on the first end of the rotatable shaft, the hub including a top end and a bottom end and at least first and second impeller arm slots arranged vertically and extending from the top end toward the bottom end;
      (iii) at least first, second, and third impeller blades extending from the hub, each of the first, second, and third impeller blades comprising a blade face, an arm having a first end and a second end and a notch between the first end and the second end, wherein the first end is adjacent to the blade face, and the second end extends into an impeller slot, the arm being engaged in the slot, wherein the second end of the first impeller blade arm engages with the notch of the third impeller blade arm, the second end of the third impeller blade arm engages with the notch of the second impeller blade arm, and the second end of the second impeller blade arm engages with the notch of the first impeller blade arm; and
      (iv) a housing assembly coupled to the bottom wall of the biocontainer, the housing assembly sealingly supporting the rotatable shaft, wherein the second end of the shaft passes through the housing assembly.

2. The bioprocessing unit of claim 1, wherein the impeller comprises rivets or bolts fixing each arm to the hub.

3. The bioprocessing unit of claim 1, further comprising a hub cap engaged with the top end of the hub.

4. A method for preparing a mixed fluid used in bioprocessing comprising
   passing at least one fluid and at least one component to be mixed with the fluid through at least one port into a biocontainer of a bioprocessing unit, the bioprocessing unit comprising:
   (a) the biocontainer, which comprises a closed container having an interior volume suitable for containing fluid, the container comprising a bottom wall, a top wall, at least one side wall, the at least one side wall being joined to the top wall and the bottom wall; and at least an inlet port, and a drain port, the drain port being arranged in the bottom wall, wherein the biocontainer further comprises:
   (b) a rotatable agitator comprising
      (i) a rotatable shaft comprising a cylindrical element having a first end and a second end, the shaft having a vertical rotational axis, the shaft passing through the bottom wall of the biocontainer such that the second end extends exterior to the bottom wall;
      (ii) an impeller comprising a hub mounted on the first end of the rotatable shaft, the hub including a top end and a bottom end and at least first and second impeller arm slots arranged vertically and extending from the top end toward the bottom end;
      (iii) at least first, second, and third impeller blades extending from the hub, each of the first, second, and third impeller blades comprising a blade face, an arm having a first end and a second end and a notch between the first end and the second end, wherein the first end is adjacent to the blade face, and the second end extends into an impeller slot, the arm being engaged in the slot, wherein the second end of the first impeller blade arm engages with the notch of the third impeller blade arm, the second end of the third impeller blade arm engages with the notch of the second impeller blade arm, and the second end of the second impeller blade arm engages with the notch of the first impeller blade arm; and
      (iv) a housing assembly coupled to the bottom wall of the biocontainer, the housing assembly sealingly supporting the rotatable shaft, wherein the second end of the shaft passes through the housing assembly; and
   rotating the impeller, and mixing the at least one fluid and the at least one component to be mixed with the fluid, and producing the mixed fluid.

* * * * *